United States Patent [19]

Bradley-Moore

[11] 4,015,592

[45] Apr. 5, 1977

[54] NUCLEAR MEDICINE SYSTEM FOR IMAGING RADIATION

[76] Inventor: Patrick Ralph Bradley-Moore, 510 E. 86th St., New York, N.Y. 10028

[22] Filed: June 12, 1975

[21] Appl. No.: 586,170

Related U.S. Application Data

[63] Continuation-in-part of Ser. No. 536,200, Dec. 24, 1974, abandoned.

[52] U.S. Cl. .............................. 128/2 A; 128/2 V; 250/303; 250/363 S
[51] Int. Cl.$^2$ ........................................ A61B 6/00
[58] Field of Search ...... 128/2 A, 2 R, 2 V, 2.05 Z, 128/4–8; 250/303, 363 S

[56] References Cited

UNITED STATES PATENTS

| | | | |
|---|---|---|---|
| 3,437,747 | 4/1969 | Sheldon | 128/4 |
| 3,465,145 | 9/1969 | Leiter | 128/2 A |
| 3,500,820 | 3/1970 | Almen | 128/2 A |
| 3,665,916 | 5/1972 | Kobayashi et al. | 128/2 A |
| 3,670,719 | 6/1972 | Kobayashi et al. | 128/2 A |
| 3,730,632 | 5/1973 | Chikama | 128/6 |

OTHER PUBLICATIONS

Hindel et al., "Multicrystal Scanner. . . Versatile," Nucleonics, Mar. 1967, pp. 52–57, vol. 25, No. 3.
Kashio et al., "Transverse Section Scanning . . . Images," Toshibe Review, Sept. 1973, pp. 34–39.

Primary Examiner—Robert W. Michell
Assistant Examiner—Lee S. Cohen
Attorney, Agent, or Firm—Cooper, Dunham, Clark, Griffin & Moran

[57] ABSTRACT

Disclosed is a system for forming a two-dimensional nuclear radiation image at a location inside an animal body and for transmitting a representation of the two-dimensional image to a location outside the body. In examining an animal body in accordance with the invention, a selected portion of the body is caused to form a nuclear radiation pattern, as by the ingestion or injection of a substance which gives out gamma radiation or by irradiation from an external source. The front end of an invented device is introduced into the body, as by way of a body cavity, to form a two-dimensional image of this nuclear radiation pattern. The middle part of the invented device transmits a representation of this two-dimensional image to the back end of the device, which is at a location outside the animal body which is being examined, where this representation forms an image of the selected animal body portion that can be viewed, recorded or otherwise utilized. The invented technique is used on a number of different devices, suitable for forming images under different conditions.

21 Claims, No Drawings

U.S. Patent   April 5, 1977   Sheet 1 of 4   4,015,592
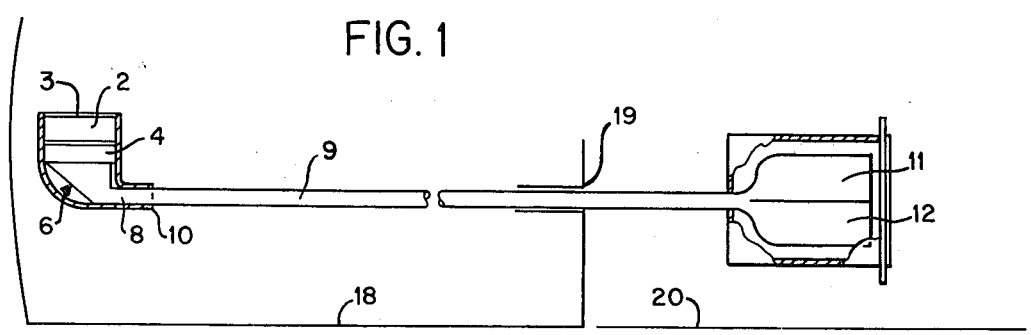
FIG. 1
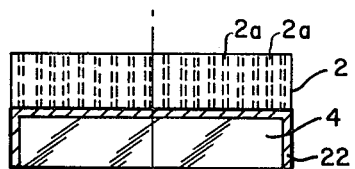
FIG. 2
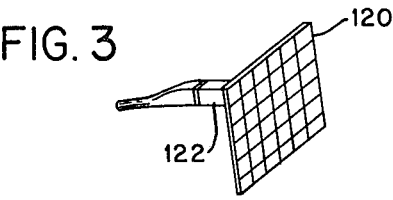
FIG. 3
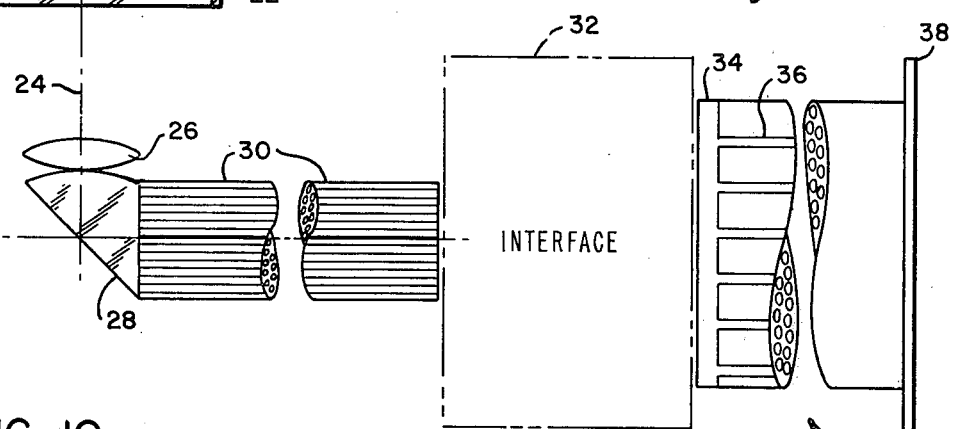
FIG. 10
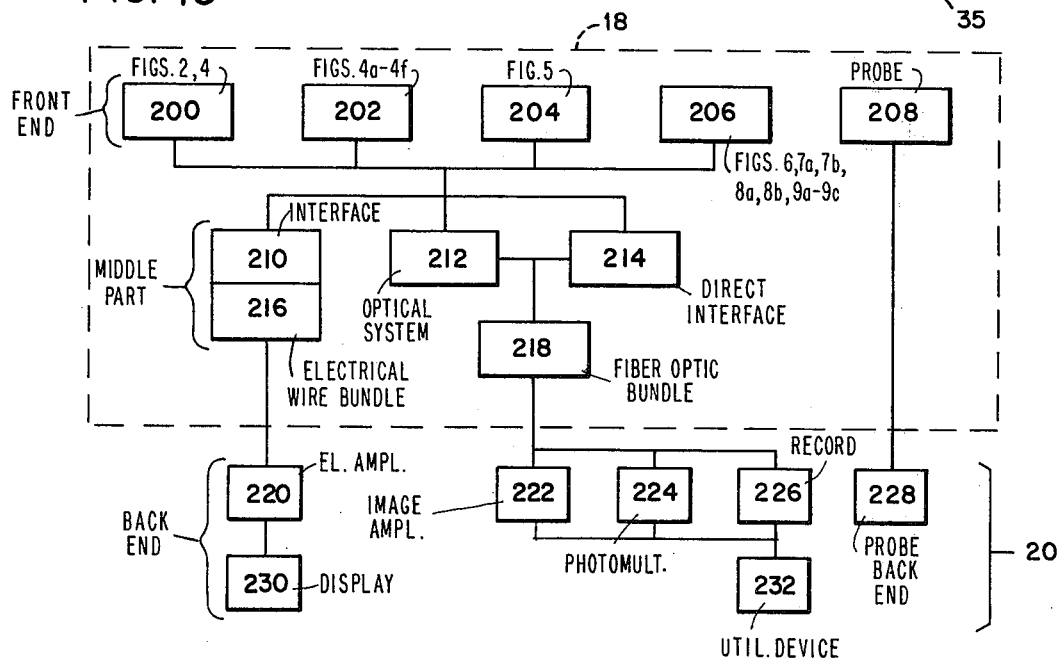

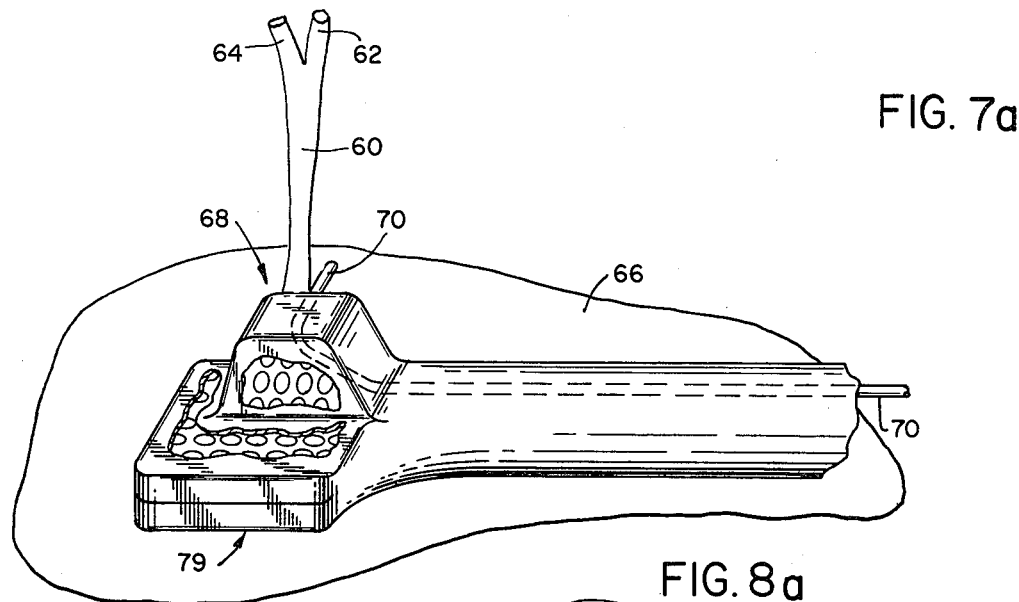
FIG. 7a
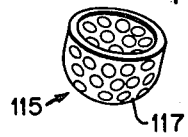
FIG. 8a
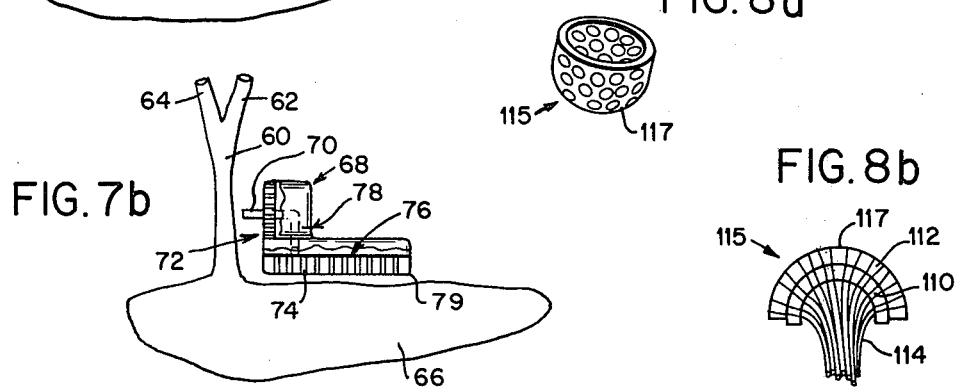
FIG. 7b
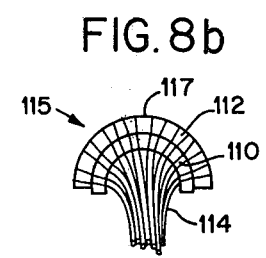
FIG. 8b
FIG. 5
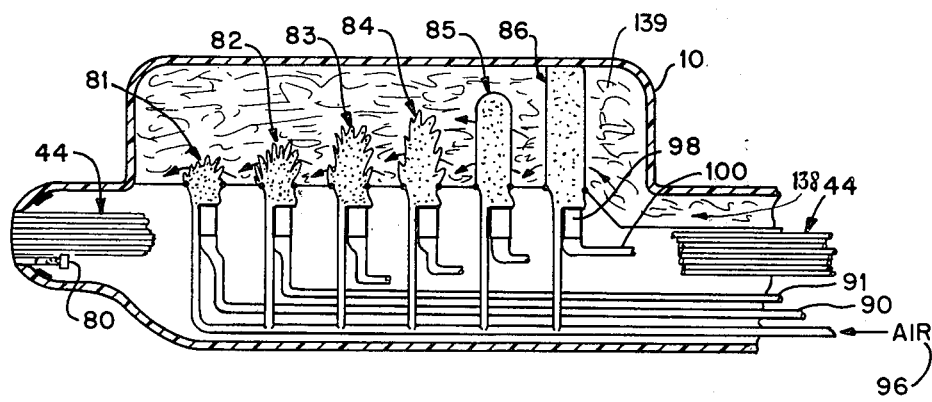

NUCLEAR MEDICINE SYSTEM FOR IMAGING RADIATION

REFERENCE TO A RELATED APPLICATION

This application is a continuation-in-part of the earlier application of the applicant herein entitled In-Body Cavitary Ionizing Radiation Detector filed on Dec. 24, 1974, under Ser. No. 536,200, now abandoned. Applicant hereby incorporates by reference into this specification all of the subject matter disclosed or claimed in said earlier application.

BACKGROUND OF THE INVENTION

The subdivision of medical practice called nuclear medicine has developed rapidly, primarily through the availability of imaging devices such as scanners, and particularly the Anger camera, the latter often associated with a computer. Such imaging devices are generally costly, large, have limited flexibility, can not be relocated readily, and can form images of internal organs only by detecting radiation which has passed through intervening tissue to reach a detector located outside the body which is being examined. Such intervening tissue scatters the nuclear radiation rays and thus degrades the image, reduces the signal-to-noise ratio by adding extraneous rays which appear to come from the area in question, and enforces, by its physical bulk, a more distant view to be taken. In addition to these disadvantages, the relationship of the area of interest to the rest of the body may prohibit a view being obtained at all, owing to the bulk and inflexibility of the currently used external detectors. Additionally, further degrading of the image results from respiratory and other motions of the imaged body organs.

Prior art devices have been used to optically view internal organs (U.S. Pat. Nos. 3,253,524; 3,799,150 and 3,799,151), and there have been suggestions to detect the presence or absence of ionizing radiation with a device implanted or otherwise introduced into an animal body. However, while optical two-dimensional images of examined organs have been obtained by such prior art devices, and while there have been suggestions that it is possible to detect the presence or absence of nuclear radiation at a location inside an animal body, it has not been possible prior to this invention to obtain a two-dimensional nuclear radiation image at a location inside an animal body and to view or otherwise utilize a representation of such two-dimensional image at a location outside the body.

SUMMARY OF THE INVENTION

The invention is in the field of nuclear medicine and relates to imaging nuclear radiation patterns and particularly to forming a two-dimensional nuclear radiation image at a location inside an animal body and for transmitting a representation of such image to a location outside the body, where it can be viewed or otherwise utilized. The images obtained in accordance with the invention typically have better resolution and give greater detail than images obtained by prior art techniques for imaging nuclear radiation, and the invention is of particular importance to imaging small, deep organs, larger paired organs and small parts of deep large organs. Such categories of organs, which may be of vital importance to the welfare and safety of patients, are inadequately imaged by prior art methods. This invention, however, allows obtaining detailed views of such organs, to thereby allow viewing and detecting conditions such as an adenoma of an adrenal, a renal mass, a renal arterial stenosis or small neoplastic metastases situated on the undersurface of the left lobe of the liver, and the like.

In one specific embodiment, a selected portion of an animal body is caused to form a nuclear radiation pattern, as by irradiating the portion with gamma rays from outside the body or by injecting or ingesting into or near the selected portion of the body a substance emitting gamma radiation. A device constructed and operating in accordance with the invention is introduced into the animal body, for example, through a body cavity, such that a front end thereof is at a location inside the body which is sufficiently close to the radiation pattern of interest. The front end of the device contains a nuclear radiation detector capable of forming a two-dimensional image of the nuclear radiation pattern of interest, and forms such an image. A representation of the formed two-dimensional image of the nuclear radiation pattern of interest is transmitted by a middle portion of the invented device to the back end of the device, which is at a location outside the body, to define at such location outside the body a two-dimensional image of the nuclear radiation pattern of interest. This image outside the body may be viewed, recorded or otherwise utilized.

The invented device may have means for steering and precisely positioning the front end as it is introduced into the animal body. The front end may have two (or more) nuclear radiation pattern detectors, each of which forms a two-dimensional image of the nuclear radiation pattern of interest from the same or a different viewing angle. A representation of each of these two-dimensional images may be transmitted to a location outside the body, to thereby provide either two- or three-dimensional views of the nuclear radiation pattern of interest. The front end of the invented device may have a radiation source emitting a selected nuclear radiation pattern that can be viewed from outside the animal body to ascertain the position and orientation of the front end of the invented device, and to thus assist in correctly positioning the two-dimensional detector contained in the front end of the device and to help interpret the image obtained thereby. The front end of the device may be solid, or may be collapsible, for easier introduction into a body cavity, where it may be expanded to detect an image, and subsequently again collapsed for withdrawal. Where the front end has two (or more) detectors, each forming a two-dimensional image, each detector may be independently controllable for movement with respect to the other, to thereby select a desired relative orientation of the detectors while the front end is inside the body.

BRIEF DESCRIPTION OF THE DRAWINGS

FIG. 1 is a schematic view of an embodiment of the invented device.

FIG. 2 is an enlarged, partial schematic view of the device shown in FIG. 1.

FIG. 3 is a perspective view of a modified detail of the device shown in FIG. 2.

FIG. 5 is a sectional view of another alternate front end of the device shown in FIG. 1.

FIG. 7a is a partly perspective and partly sectional view of an alternate device for forming three-dimensional views of a nuclear radiation pattern, and FIG. 7b is a partly elevational and partly sectional view of a detail of the device shown in FIG. 7a.

FIGS. 8a and 8b are respectively a perspective view of a collimator and a schematic view of another device for forming a three-dimensional view of a selected nuclear radiation pattern.

FIG. 10 is a diagram illustrating certain combinations between alternate portions forming a device of the type illustrated in FIG. 1.

DETAILED DESCRIPTION

Figure 4A:
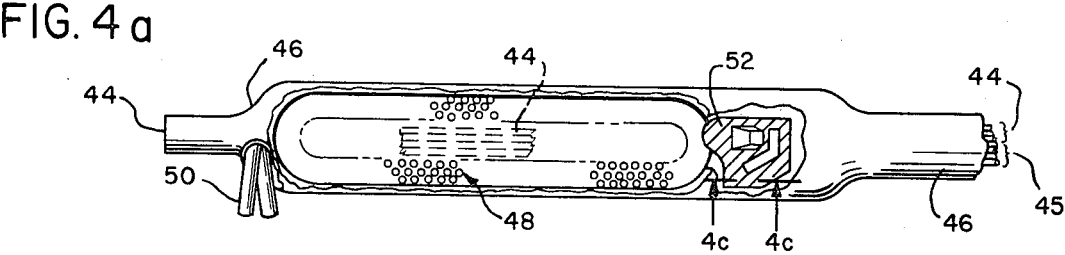
FIGS. 4a, 4b and 4c are partly elevational and partly sectional views of an alternate front end of the device shown in FIG. 1.

Referring to FIG. 1, the invented device comprises a front end for forming a two-dimensional image of a radiation pattern inside an animal body, a middle part for guiding the front end and for transmitting a representation of the formed two-dimensional image of a nuclear radiation pattern to a location outside the body, and a back end disposed at a location outside the animal body and comprising controls for guiding and positioning the front end and means for utilizing the representation of the two-dimensional image transmitted to the location outside the animal body.

More specifically, the front end comprises a collimator 2 for collimating a nuclear radiation pattern entering through its front face 3, a two-dimensional nuclear radiation detector 4 and an optical system 6 for directing the image formed by the radiation detector 4 into the middle part of the device. The front end is within a cover 10, which is sterile and impervious, and which may cover the entire portion of the device inserted into an animal body. The middle part of the device comprises a fiber optic bundle 8 interfaced at one end to the optical system 6 to receive therefrom the image formed by the radiation detector 4, and a control conduit 9 running along the fiber optic bundle 8 and secured at its front portion to the front end of the device. The front end of the device and a forward portion of the middle part are introduced through an orifice schematically shown at 19 into an animal body whose outline is schematically shown at 18, such that a back portion of the fiber optic bundle and the back portion of the control conduit 9 (and perhaps of the cover 10) extend outwardly of the animal body 18 into an area schematically illustrated at 20, where the back portion of each of the fiber optic bundle 8 and the control conduit 9 is connected to the back end of the device. This back end comprises a control portion 11 containing controls for interacting with the control conduit 9, and a portion 12 for viewing or otherwise utilizing the representation of the nuclear radiation pattern transmitted by the middle part from the front end of the device.

In use of the device shown in FIG. 1, the front end is typically introduced through an existing orifice 19 into a cavity of a body 18, in the manner typically used with endoscopes, and is guided to a suitable position and orientation with respect to a selected body portion with the help of the control conduit 9 and the controls 11. The two-dimensional nuclear radiation pattern at the front face 3 of the collimator 2 is converted to an optical two-dimensional image by the radiation detector 4, and this optical two-dimensional image is transmitted to the location 20 outside the animal body by the optical system 6 and the fiber-optic bundle 8. Typically, the optical image is not an instantaneous one, but results from the cumulative effect of successively detected radiation quanta. The portion 12 of the back end of the device receives this optical image and may display it, with or without image enhancement, or may otherwise utilize it.

Referring to FIG. 2, which shows an enlarged partial view of the device shown in FIG. 1, the collimator 2 is made of a material such as lead and is generally cylindrical and has a plurality of parallel, axially extending, circular, closely packed passageways 2a. For example, the collimator 2 may have a diameter of approximately 2.5 centimeters and the passageways 2a may be 0.5 millimeters in diameter and may be packed hexagonally, with center-to-center distance of 1.5 millimeters. The thickness of the collimator 2 may be about 0.5 centimeters. A radiation detector 4 is coaxially disposed below the collimator 2, and may comprise a solid crystal of thallium-activated sodium iodide having a nonreflective coating 22 over its top and sides but optically open along an optical axis 24 to an optical system comprising a light collecting and bending lens 26 and a prism 28. The image of the nuclear radiation pattern at the front end 3 of the collimator 2 is converted to an optical image by the radiation detector 4, and this optical image is focused on the reflecting face of the prism 28 by the lens 26 and is reflected by the prism 28 into the entrance ends of the fibers comprising the fiber-optic bundle 30. This optical image is transmitted by the fiber-optic bundle 30 to a location outside the body, where the exit ends of the fibers making up the bundle 30 apply the transmitted optical image to an image amplifier 35 through an interface 32. The image amplifier 35 comprises an input end 34, a middle portion 36 comprising a plurality of parallel tubes for image amplification, and a screen 38 for viewing the amplified optical image. Other utilization means, such as photographic cameras, recorders, or image processing devices (not shown) may be suitably secured to the image amplifier 35 to record or otherwise utilize the image displayed thereon. For simplicity, FIG. 2 does not show a sterile cover for the portion of the device inserted into the animal body or the control conduit 9 and the control portion 11 of the back end of the device.

Instead of the unitary image amplifier 35, the device shown in FIG. 2 may have a back end of the type illustrated in FIG. 3 and comprising a bundle of photo-multiplier tubes 122 (only one is shown) each connected at its input to receive the optical image at the outlet end of a single fiber from the fiber-optic bundle 30 in FIG. 2, or the optical images from two or more fibers. The output end of each photo-multiplier tube 122 forms a square of a display array 120, where the resulting two-dimensional image may be viewed, photographed or otherwise utilized.

Figure 4B:
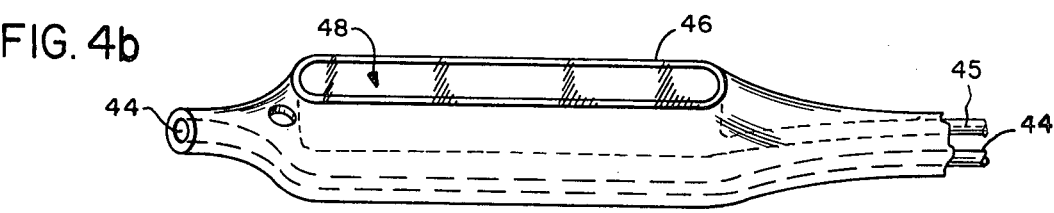
Figure 4C:
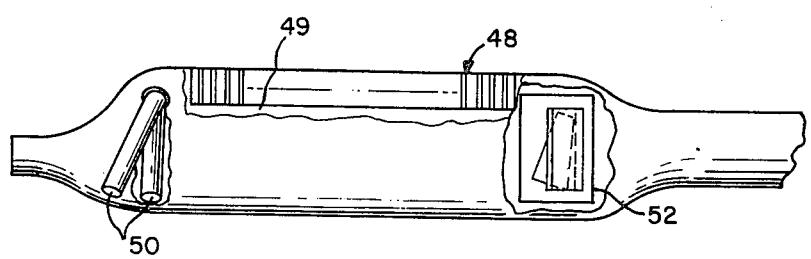
Figure 4D:
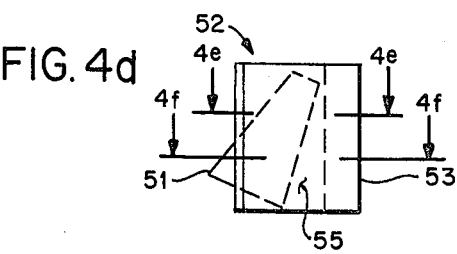
FIGS. 4d, 4e and 4f are enlarged views of a detail of the device shown in FIGS. 4a, 4b and 4c.
Figure 4E:
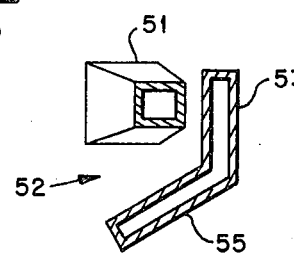
Figure 4F:
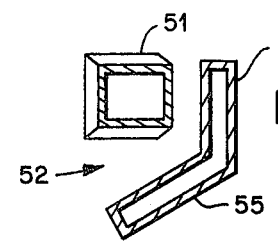

FIGS. 4a through 4f illustrate a front end which may be used instead of the front end of the devices shown in FIGS. 1 and 2. Referring to FIGS. 4a, 4b and 4c, the alternate front end comprises an elongated outer cover 46 which receives at its back end (the right-hand side of the drawing) a fiber optic bundle 44 and another fiber optic bundle 45. The fiber optic bundle 44 proceeds through the length of the cover 46 and optically opens forward at the front surface of the device (at the left-hand side of the drawing). The fiber optic bundle 44 is for optically looking forward, serving as in an optical endoscope. Some of the fibers of the bundle 44 may be used for transmitting illuminating light while others are used for viewing the environment illuminated by such light; alternately, a separate light source (not shown) may be added to the device and the entire fiber optic bundle 44 may be used for viewing the environment illuminated by such light source. The fiber optic bundle 44 extends to the back end of the device, where it interfaces with a suitable viewing screen (not shown) of the type typically used with optical endoscopes. The fiber optic bundle 45 is similar to the fiber optic bundle 30 in FIG. 2, and interfaces in a similar manner with an optical system (not shown) corresponding to the one shown in FIG. 2, to receive the optical image formed in a crystal 49 disposed under a collimator 48. The collimator 48 and the detector 49 correspond to the collimator 2 and detector 4 in FIG. 2, but are oblong in shape rather than circular. For the purpose of assisting in guiding and positioning the shown front end inside an animal body, and for assisting in interpreting the resulting nuclear radiation image, the shown front end includes a radiation source comprising a pair of tubes 50 and a radiation source 52 comprising a truncated pyramid 51 and an angled plate comprising sections 53 and 55. Each of the elements 50, 51, 53 and 55 includes radiation material and provides a radiation pattern capable of traversing the animal body under examination so as to be detected at a location outside the body. Referring to FIGS. 4d, 4e and 4f, the shapes of the elements 51, 53 and 55 are such that an image of the radiation provided by these elements and viewed outside the body indicates by its shape and size the position and orientation in the body of the front end of FIGS. 4a–4c.

The radiating material of the element 51 is only at the bottom of the pyramid, while the remainder of the pyramid is made of a material such as lead, so that the radiation pattern emitted through the open small end of the element 51 is in the form of a pyramid having a square cross-section. When viewed at a detector (not shown) outside the body, a square view would indicate that the detector plane is parallel to the top of the pyramid and the size of the square image would indicate the distance between the element 51 and the detector. Any distortion from a square shape would indicate the angle between the plane of the detector and the top of the pyramid 51. Similarly, the elements 53 and 55 may have radiating material only in one of the narrow sides (i.e., a side which is in the plane of the drawing in FIGS. 4e and 4f) while the large walls are of a material such as lead and the narrow wall opposite the radiating wall is open. Thus, the shape and size of the radiation pattern emitted by the elements 53 and 55 and viewed outside the body would indicate the position and orientation of the front end of FIGS. 4a–4c. The radiation source 50 may comprise two tubes, each radiating a pattern along a different axis, or may comprise a single tube or more than two tubes. The radiation patterns from the element 50, 51, 53 and 55 may be used either individually or in conjunction to find the position and orientation of the front end; a front end may have all of the discussed radiation sources or a subset thereof.

In some cases, there may be severe limitations on the size of the front end, at least while the front end is being inserted into the body and guided to its desired final position. An alternate front end, of the type illustrated in FIG. 5, is particularly well suited to such situations. The front end of FIG. 5 is enclosed in an external covering 10 made of flexible material and enclosing a hollow chamber 139 communicating with the back end of the device through a conduit 138. The cover 10 also encloses a plurality of inflatable bags 81 through 86 communicating with the back end of the device through an air conduit 96. At the base of each inflatable bag there is a crystal detector (detector 98 is labeled) communicating with the back end of the device through an optical fiber 100. A small optical system, such as a prism (not shown), may interface the crystal 98 and the fiber 100 in a manner similar to that discussed in connection with FIGS. 1 and 2. In operation of the device shown in FIG. 5, the chamber 139 is empty and the inflatable bags are deflated, to collapse the cover 10 and reduce the sectional area of the device for easier insertion into a body cavity. The front end of FIG. 5 is guided to a desired final location, by itself or by means of a control conduit (not shown) of the type discussed in connection with FIG. 1, until the desired final location and orientation are reached. Then mercury is pumped through the conduit 138 from the back end into the chamber 139 to expand the cover 10 to the shape illustrated in FIG. 5 and air is pumped into the inflatable bags from the back end through the air conduit 96 to expand each of the air bags to the shape of the air bag 86 shown in the figure. As a result, the mercury forms a collimator serving the function of the collimator 2 in FIGS. 1 and 2 and the inflated air bags form passageways through the collimator through which a radiation pattern can be detected by the crystal detectors 98. The fibers 100 form a fiber optic bundle (of which only fibers 90 and 91 are shown) for transmitting the optical images formed at the crystals 98 to the back end of the device. Additionally, there may be a fiber optic bundle 44 which is optically open at the front end of the device (the left-hand side in FIG. 5) to view the environment illuminated by a bulb 80 and transmit an optical image thereof to the back end of the device. After the desired nuclear radiation patterns have been imaged, the mercury is pumped out of the chamber 139 through the conduit 138 and the bags are deflated through the air conduit 96, to thereby collapse the illustrated front end for easier withdrawal from the examined body.

Figure 6:
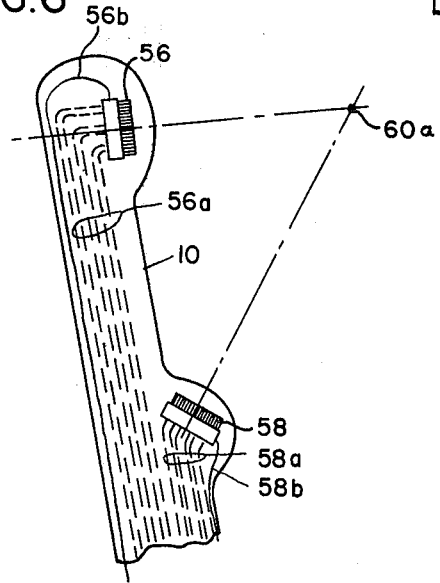
FIG. 6 is a schematic view of another modification of the front end of the device shown in FIG. 1, allowing forming three-dimensional views of a selected nuclear radiation pattern.

In certain cases it may be desirable to view more than one radiation pattern, so as to view the same organ from more than one viewing angle, or to view more than one organ, etc. A front end for the invented device suitable to such cases is illustrated in FIG. 6, where a cover 10 encloses a first radiation detector 56 having a suitable collimator and connected to a back end through a fiber optic bundle 56a and a second radiation detector 58 having a suitable collimator and connected to a back end through a fiber optic bundle 58a. Each of the radiation detectors 56 and 58 can be similar to any of the front ends discussed above, and each forms a two dimensional image of a radiation pattern and transmits this image to a back end of the type discussed above through its fiber optic bundle. In the illustration of FIG.

6 the radiation detectors 56 and 58 view a single object 60a from different angles, but it should be clear that the radiation detectors 56 and 58 may be pointed along different directions to view different radiation patterns and different organs or different parts of the same organ. The orientation of each of the detectors 56 and 58 is independently controlled by control conduits 56b and 58b, respectively, connected to suitable control panels (not shown) outside the body which are of the type commonly used in connection with endoscopes.

A more specialized front end for viewing two different radiation patterns is illustrated in FIS. 7a and 7b and is particularly suited to viewing two organs which are not in the same plane, for example, for viewing the pancreas 66 and the common bile duct. Referring to FIGS. 7a and 7b the illustrated front end comprises: a first portion 7a having a collimator 74 and a crystal detector 76 for viewing the pancreas 66, forming a two-dimensional image of the radiation pattern thereof and transmitting this image through a fiber optic bundle (not shown) to a back end; and a second portion 68, at a right-angle to the first portion 79 and comprising a collimator 72 and a detector 78 for viewing the ducts 60, 62 and 64, forming a two-dimensional image thereof and transmitting this two-dimensional image to a back end through a fiber optic bundle (not shown). The shown front end may include an ultrasonic probe 70 suitably communicating with a back end and any other of the front end portions discussed above, such as a control conduit (not shown) for guiding and positioning the illustrated front end, radiation sources (not shown) for ascertaining the position and orientation of the front end, and the like.

An alternate front end is illustrated schematically in FIGS. 8a and 8b and is particularly suited to obtaining a panoramic view of radiation pattern. Specifically, the alternate front end 115 of FIGS. 8a and 8b comprises a hemispheric collimator 112 having radial passageways and a similarly shaped crystal detector 110 fitting inside the collimator 112 to convert radiation entering the collimator passageways from its front face 117 into an optical image. This optical image is conveyed to a back end of the device through a fiber optic bundle 114 interfacing with the crystal detector 110.

Figure 9A:
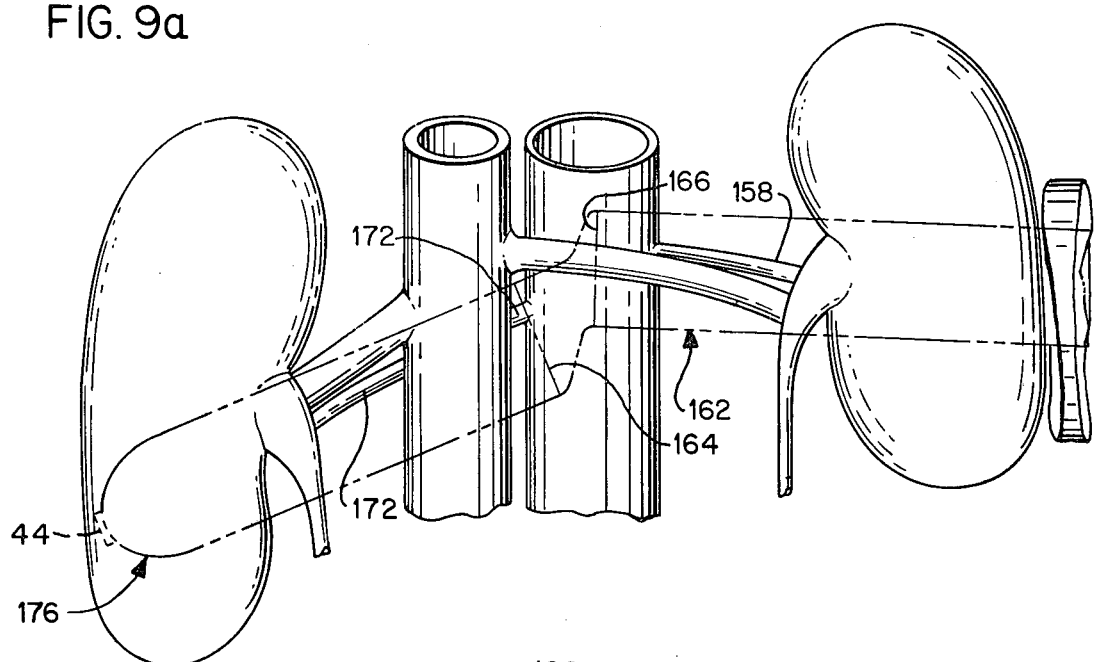
FIGS. 9a, 9b and 9c illustrate schematically another device for forming a three-dimensional view of a selected nuclear radiation pattern comprising two detectors selectively movable with respect to each other.
Figure 9B:
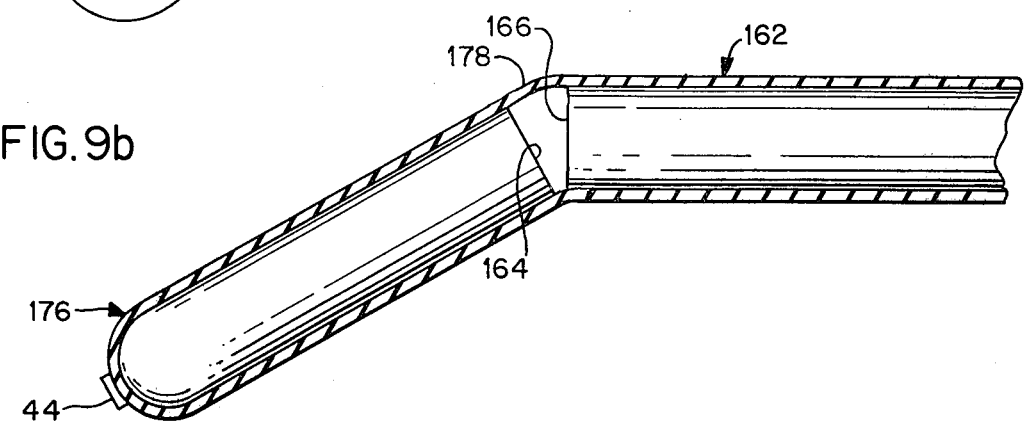
Figure 9C:
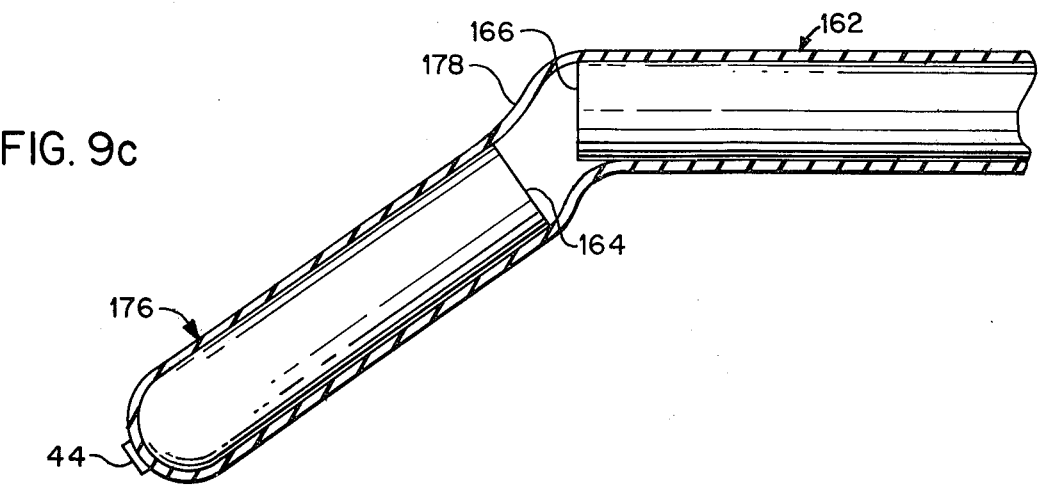

A still alternate front end is shown in FIGS. 9a–9c and is particularly suited to viewing the right and left renal arteries 172 and 158 as specifically illustrated in FIG. 9a. Referring to FIGS. 9a–9c, the front end comprises a first radiation detector 164 and a second radiation detector 166 disposed in succession at respective portions 176 and 162 of a flexible tubular cover 178. Each of the detectors 164 and 166 may comprise a collimator and a crystal detector communicating optically with a fiber optic bundle, thus forming and transmitting to a back end a two-dimensional image of a radiation pattern in the manner discussed in connection with FIGS. 4a–4c. While the optical systems and fiber optic bundles of the detectors 164 and 166 are omitted for simplicity in FIGS. 9a–9c, it should be clear that they are in fact present and are used in the same manner as the fiber optic bundle 30 in FIG. 2. Additionally, there may be a third fiber optic bundle 44, of the type discussed in connection with FIGS. 4a–4c, and there may be a control conduit, of the type of the control conduit 9 discussed in connection with FIG. 1. The detectors 164 and 166 may be spaced from each other along the length of the flexible tube 178 so that the tube may bend to form an angle between the detectors of the type illustrated in FIG. 9b, or to additionally space the detectors transversely from each other as illustrated in FIGS. 9a and 9c. Each of the detectors 164 and 166 can be independently related and moved along the tube 178 and oriented with respect to the other detector by an independent endoscope-type control (not shown) controlled from outside the body.

The device portions discussed above may be combined in different manners to form different devices for carrying out the invention. Referring to FIG. 10, any of the vertical paths from 200, 202, 204 and 206 may be followed to a utilization device 230 or 232 to form a complete device in accordance with the invention. Thus, 200 represents the front end which is illustrated in FIGS. 2 and 4 and comprises a collimator 2 and a crystal detector 4, and this may be combined with a suitable middle part and a suitable interface to the chosen middle part, and, ultimately, to a suitable back end. For example, the collimator and crystal detector of 200 can be combined with an interface 210 and a middle part 216, where the interface 210 may comprise an array of photo diodes (not shown) each viewing a portion of the radiation detector 4 and converting to an electrical signal any optical signal formed in the radiation detector due to detected radiation, and the middle part 216 may comprise a bundle of electrical wires connecting the photo diodes to a back end, in which case the back end 220 would be an electrical amplifier amplifying the electrical signals applied from the photo diodes, and 230 would be any suitable utilization device, such as a CRT display, which may additionally have a photographic camera or the like. Alternately, the collimator and radiation detector of 200 can be interfaced through an optical system 212, comprising the lens 26 and prism 28 of FIG. 2, with a middle part 218, comprising the fiber optic bundle 30 of FIG. 2, and with a back end which may be any of 222, 224 or 226. 222 may be the image amplifier 35 of FIG. 2, 224 may be the photo multiplier array of FIG. 3 and 226 may be any suitable recorder. 222, 224 and 226 are connected to a utilization device 232 which may be, for example, a photo camera or a suitable image processor. Still alternately, the collimator 2 and radiation detector 4 of 200 may be connected through an interface 214 with the middle part 218, where the interface 214 represents simply a direct connection between the radiation detector crystal and the fiber optic bundle, without any optical system of the type of the lens 26 and the prism 28 of FIG. 2, as illustrated schematically in FIG. 6. 202 represents the front end illustrated in FIGS. 4a–4f and it may form a combination with the remaining portions of the device along any of the indicated vertical paths. 204 represents a front end of the type illustrated in FIG. 5, and it, too, may be connected with remaining devices along any of the indicated vertical paths in FIG. 10. It is noted that the individual crystals 98 in FIG. 5 may be interfaced with fibers, for conveying optical images, or may be interfaced with photo diodes each connected to a back end with a wire. 206 represents any of the remaining front ends (i.e., of FIGS. 6, 7a and 7b, 8a and 8b, and 9a–9c) and may be combined along any of the indicated vertical paths. 208 represents a portion of a front end which does not serve to form two-dimensional images of radiation patterns, and it may be, for example, an ultrasonic probe of the type illustrated in FIGS. 7A and 7B, a fiber optic bundle for forming optical images of the type shown in FIGS. 4A–4C, or a control conduit of the type discussed in connection with FIG. 1, or any similar device which may be combined with the radiation image forming devices discussed above. The device of 208 is connected to a suitable conduit with a back end 228 of a suitable type, e.g., a back end for an ultrasonic probe, a back end for a control conduit, a back end for an optical endoscope, etc.

I claim:

1. A nuclear medicine device for forming a nuclear radiation image at a location inside an animal body and for transmitting a representation of said image to a location outside the body comprising:
   a front end comprising means for forming, at a location inside an animal body, a two-dimensional image of a selected nuclear radiation pattern; and
   a middle part comprising means interfacing with the front end to receive therefrom a two-dimensional representation of the nuclear radiation pattern image formed therein and adapted to extend to a location outside the body to transmit the received two-dimensional representation thereto.

2. A nuclear medicine device as in claim 1 wherein: said means for forming a two-dimensional image comprise means including a collimator for collimating the nuclear radiation pattern and means including a crystal detector for converting the collimated nuclear radiation pattern to a two-dimensional optical image; and said middle part comprises means for receiving said two-dimensional optical image from the converting means and for transmitting the received optical image to said location outside the body.

3. A nuclear medicine device as in claim 2 wherein the means for receiving and transmitting said optical image comprise a fiber optic bundle interfacing with the converting means to receive the optical image therefrom and transmitting said optical image to the location outside the body.

4. A nuclear medicine device as in claim 1 wherein the means for forming a two-dimensional image comprise a flexible tubular cover having an inflatable cavity, means for selectively inflating the cavity with a material which is substantially opaque to the imaged nuclear radiation, a plurality of inflatable bags which are located substantially inside the cavity and which, when inflated, extend across the inflatable cavity parallel to each other, and means for inflating the bags with a material which is transparent to the imaged nuclear radiation pattern, to form thereby a collimator by inflating the cavity and the bags at a location inside the body, and radiation detector means disposed in the tubular cover to form a two-dimensional image of the nuclear radiation pattern traversing the collimator.

5. A nuclear medicine device as in claim 1 wherein the front end further comprises means for forming an auxiliary radiation pattern detectable at a location outside the body.

6. A nuclear medicine device as in claim 5 wherein the means for forming said auxiliary radiation pattern include means for forming an auxiliary pattern of a selected shape.

7. A nuclear medicine device for forming nuclear radiation images at locations inside an animal body and for transmitting representations of said images to locations outside the body, comprising:
   a front end comprising first means for forming, at a location inside the body, a first two-dimensional image of a selected nuclear radiation pattern and a second means for forming, at a location inside the body, a second two-dimensional image of a selected nuclear radiation pattern; and
   a first middle part and a second middle part having means for interfacing respectively with the first means for forming an image and the second means for forming an image to receive the respective formed images and adapted to extend to respective locations outside the body to transmit the received images thereto.

8. A nuclear medicine device as in claim 7 wherein each of said first and second means for forming a two-dimensional image comprise means including a collimator for collimating a nuclear radiation pattern and means including a crystal detector for converting the collimated nuclear radiation pattern to a two-dimensional optical image.

9. A nuclear medicine device as in claim 7 wherein the front end comprises means for selectively orienting the first and second means for forming a two-dimensional image at a selected solid angle with respect to each other.

10. An apparatus for forming an external image of areas of interest defined by tissue-penetrating ionizing radiation inside an animal body, said apparatus comprising in combination:
    a. detector means for forming a substantially continuous two-dimensional potential image by the detection of said radiation, said detector means formed and sized to be introducible into said animal body;
    means for introducing the detector means into said animal body;
    c. means for attenuation of said radiation prior to the detection thereof by the detecting means to reduce the radiation incident on the detecting means except from selected directions;
    d. means for passage of the information content of a selected two-dimensional representation of said potential image to a location outside said animal body; and
    e. means for changing said information content of the selected two-dimensional representation of the potential image into an interpretable form.

11. An apparatus as in claim 10 in which said introducible detector means has associated therewith means for identification of the locality of the detector means inside the body.

12. An apparatus as in claim 10 where said means for passage of the information content includes means for increasing the intensity of the information content of said potential image.

13. An apparatus as in claim 10 wherein said detector means include means responsive to other than said ionizing radiation for obtaining information from a region inside said animal body accessible to said detector means, and including means for passage of the last recited information to a location outside said animal body and for utilizing said last recited information.

14. An apparatus as in claim 10 wherein said detector means includes means for providing a therapeutic treatment to a region inside said animal body accessible to said detector means.

15. An apparatus as in claim 10 wherein said detector means and said means for attenuation each include means for alteration of the geometry thereof.

16. An apparatus as in claim 10 in which said detector means comprises semiconductor material; said means for passage is comprised of means for conduction of electricity; and said means for changing said information content accepts said information content in an electrical form.

17. An apparatus as in claim 14 in which said detector means is comprised a selected one of scintillator material and semiconductor material; said passage means comprises fiber-optic means; and said means for changing said information content accepts said information content in an optical form.

18. A nuclear medicine method of examining a selected portion of an animal body comprising the steps of:
   causing said selected portion of the body to form a nuclear radiation pattern;
   introducing into the animal body a device for detecting nuclear radiation and forming by said device, at a location inside the body, a two-dimensional image of said nuclear radiation pattern; and
   transmitting a two-dimensional representation of said image formed of the two-dimensional nuclear radiation pattern to a location outside the body.

19. A nuclear medicine method as in claim 18 wherein the image forming step comprises collimating the nuclear radiation pattern and converting the collimated pattern to a corresponding two-dimensional optical image at said location inside the body, and said transmitting step comprises transmitting said optical image to the location outside the body.

20. A nuclear medicine method of examining a selected portion of an animal body comprising the steps of:
   causing said selected portion of the body to form a nuclear radiation pattern;
   introducing into the body a device for detecting nuclear radiation and forming by said device, at a location inside the body, a first two-dimensional image of the nuclear radiation pattern and a second two-dimensional image of the nuclear radiation pattern, said first image and said second image being at individually selected viewing angles with respect to the imaged nuclear radiation pattern; and
   transmitting a two-dimensional representation of each of said images formed of said two-dimensional nuclear radiation patterns to selected locations outside the body.

21. The method of externally completing the formation of an image of areas of interest located inside a structure comprising an animal body comprising the following steps:
   a. defining areas of interest using tissue-penetrating ionizing radiation in said animal body;
   b. introducing into said animal body a detector of said radiation;
   c. attenuating said radiation prior to detection by use of an attenuator of said radiation to reduce incident radiation except from selected directions;
   d. detecting said radiation so as to form a substantially continuous two-dimensional potential image in said detector;
   e. passing the information content of a selected two-dimensional representation of said potential image outside said animal body; and
   f. changing said information content into an interpretable two-dimensional image.

* * * * *